United States Patent
Hart et al.

(10) Patent No.: US 8,173,386 B2
(45) Date of Patent: May 8, 2012

(54) METHOD OF ASSAYING ENZYME-MEDIATED OXIDATIVE DEMETHYLATION

(75) Inventors: Russell Hart, Chelsea, MI (US); Barbara Scheuer, Chelsea, MI (US); Raymond Trievel, Ypsilanti, MI (US)

(73) Assignee: Arbor Assays, LLC, Ann Arbor, MI (US)

( * ) Notice: Subject to any disclaimer, the term of this patent is extended or adjusted under 35 U.S.C. 154(b) by 512 days.

(21) Appl. No.: 12/353,723

(22) Filed: Jan. 14, 2009

(65) Prior Publication Data

US 2010/0184108 A1 Jul. 22, 2010

(51) Int. Cl.
*C12Q 1/26* (2006.01)
(52) U.S. Cl. .......................... 435/25; 436/166
(58) Field of Classification Search .................... 435/25; 436/166
See application file for complete search history.

(56) References Cited

U.S. PATENT DOCUMENTS 7,416,856 B2   8/2008  Baliga et al.
2008/0220534 A1*  9/2008  Paolacci et al. ............... 436/128

OTHER PUBLICATIONS

Tsukada Y. et al. Histone Demethylation by a Family of JmjC Domain Containing Proteins. Nature 439:811-816, Feb. 16, 2006.*
Compton B. et al. Fluoral-P, A Member of a Selective Family of Reagents for Aldehydes. Analytica Chimica Acta 119(2)349-357, Oct. 1980.*
Pinheiro H. et al. Spectrofluorimetric Determination of Formaldehyde in Air After Collection Onto Silica Cartridges Coated with Fluoral P. Microchemical J 78(1)15-20, Sep. 2004.*
Collzao, E. et al., A coupled fluorescent assay for histone methyltransferases, *Analytical Biochemistry*, 342: 86-92, 2005.
Lizcano, J.M. et al., A Spectrophotometric Method for Determining the Oxidative Deamination of Methylamine by the Amine Oxidases, *Analytical Biochemistry*, 286: 75-79, 2000.
Cloos, P. et al., The putative oncogene GASC1 demethylates tri- and dimethylated lysine 9 on histone H3, *Nature*, 442: 307-311, Jul. 20, 2006.
Wang, C. et al., A general fluorescence-based couple assay for S-adenosylmethionine-dependent methyltransferases, *Biochemical and Biophysical Research Communications*, 331: 351-356, 2005.
Roy, T.W. et al., Kinetic studies of *Escherichia coli* AlkB using a new fluorescence-based assay for DNA dimethylation, *Nucleic Acids Research*, pp. 1-7, Nov. 14, 2007.
Trzaskos, J. et al., Microsomal Enzymes of Cholesterol Biosynthesis, *The Journal of Biological Chemistry*, 261(31): 14651-14657, Nov. 5, 1986.

Hollenberg, P., Mechanisms of cytochrome P450 and peroxidase-catalyzed xenobiotic metabolism, *Mechanisms of Hemeprotein Catalysis*, 6: 686-694, Jan. 1992.
McLean, K.J. et al., CYP121, CYP51 and associated redox systems in *Mycobacterium tuberculosis*: towards deconvoluting enzymology of P450 systems in a human pathogen, *Biochemical Society Transactions*, 34(6):1178-1182, 2006.
Tsukada, Y. et al., Histone dimethylation by a family of JmjC domain-containing proteins, *Nature*, 439: 811-816, Feb. 16, 2006.
Culhane, J. et al., LSD1 and the chemistry of Histone Demethylation, *Curr Opin Chem Biol*, 11(5): 561-68, Oct. 2007.
Shi, Y. et al., Histone Demethylation Mediated by the Nuclear Amine Oxidase Homolog LSD1, *Cell*, 119: 941-953, Dec. 29, 2004.
Pinheiro, H. et al., Spectrofluorimetric determination of formaldehyde in air after collection onto silica cartridges coated with Fluoral P, *Microchemical Journal*, 78:15-20, 2004.
Yin, H. et al., Methanol Solvent May Cause Increased Apparent Metabolic Instability in In Vitro Assays, *Drug Metabolism and Disposition*, 29(2): 185-193, 2001.
Wilson, J.R., Target the JMJD2A histone lysine demethylase, *Nature Structural & Molecular Biology*, 14(8): 682-684, Aug. 2007.
Couture, J. et al., Specificity and mechanism of JMJD2A, a trimethyllysine-specific histone demethylase, *Nature Structural & Molecular Biology*, 14(8): 689-695, Aug. 2007.
Chang, B. et al, JMJD6 is a Histone Arginine Demethylase, *Science*, 318(5849):444-447, Oct. 19, 2007.
Loh, H. et al., Quantitative Analysis of Formaldehyde Using UV-VIS Spectrophotometer Pattern Recognition and Artificial Neural Networks, *Analytical Letters*, 40: 281-293, 2007.
Wojciechowski, C. et al., A Continuous Fluorometric Assay for Pectin Methylesterase, *Analytical Biochemistry*, 237: 103-108, 1996.
Hamano, T. et al., Enzymic Method for the Spectrophotometric Determination of Choline in Liquor, *Analyst*, 117: 1033-1035, Jun. 1992.
Tsuchiya, H. et al., Determination of Formaldehyde in Reagents and Beverages Using Flow Injection, *Analyst*, 119: 1413-1416, Jun. 1994.
F. Oliveira et al., A sensitive flow analysis system for the fluorimetric determination of low levels of formaldehyde in alcoholic beverages, *Talanta*, 73: 561-66, 2007.
Li, Q. et al., Flow-injection spectrofluorometric determination of trace amounts of formaldehyde in water after derivtization with acetoacetanilide, *Talanta*, 72: 1675-80, 2007.

* cited by examiner

*Primary Examiner* — Ralph Gitomer

(74) *Attorney, Agent, or Firm* — Gifford, Krass, Sprinkle, Anderson & Citkowski, P.C.

(57) ABSTRACT

Methods of assaying enzyme-mediated oxidative demethylation are provided according to embodiments of the present invention which includes combining, under reaction conditions, an oxidative demethylation enzyme, a substrate for the oxidative demethylation enzyme and a formaldehyde detection reagent. Detection of fluorescence is indicative of formaldehyde generated by oxidative demethylation of the substrate by the enzyme, the fluorescence resulting from reaction of formaldehyde and the formaldehyde detection reagent.

4 Claims, 4 Drawing Sheets

LSD1-Type Demethylase

Jumonji-Type Demethylase

HDM = Histone Demethylase

METHOD OF ASSAYING ENZYME-MEDIATED OXIDATIVE DEMETHYLATION

GOVERNMENT SPONSORSHIP

This invention was made with government support under contract GM073839 awarded by NIGMS, NIH. The government has certain rights in the invention.

FIELD OF THE INVENTION

The present invention relates generally to methods and compositions for detection of formaldehyde. In specific embodiments, the present invention relates to detection of formaldehyde byproducts of enzyme activity and sensitive assays for enzyme activity.

BACKGROUND OF THE INVENTION

Formaldehyde is common byproduct formed in the oxidative demethylation of proteins, nucleic acids, and biological small molecules Conventional methods for measuring enzyme-mediated oxidative demethylation are limited and cannot be used in high throughput screening for modulators of the enzymes. For example, known assays for formaldehyde formation from a demethylase reaction involve the use of radiolabeled ($^{14}$C or $^{3}$H) methyl-peptide substrates with the subsequent formation, isolation and quantitation of radioactive formaldehyde. Alternative methods have included measurement of the formation of hydrogen peroxide as a byproduct of enzyme activity or Western blotting using methyl lysine specific antibodies. The measurement of hydrogen peroxide product to determine the activity of oxidative demethylases can be problematic in drug screening scenarios since the peroxide formed can react with the test compound or with other components of the demethylase reaction.

Despite their biological importance, oxidative demethylase enzyme activities have proven difficult to quantitatively assay hindering understanding of their kinetic properties, substrate specificities, and reaction mechanisms.

Thus, there is a continuing need for methods and compositions for detection of formaldehyde byproducts of enzyme activity and sensitive assays for enzyme activity.

SUMMARY OF THE INVENTION

Methods of assaying enzyme-mediated oxidative demethylation are provided according to embodiments of the present invention which includes combining, under reaction conditions, an oxidative demethylation enzyme, a substrate for the oxidative demethylation enzyme and a formaldehyde detection reagent. Detection of fluorescence is indicative of formaldehyde generated by oxidative demethylation of the substrate by the enzyme, the fluorescence resulting from reaction of formaldehyde and the formaldehyde detection reagent.

In particular embodiments of methods of the present invention, an oxidative demethylation enzyme activity detected is a histone demethylase activity, a DNA demethylase activity or a P450 demethylase enzyme activity. In a preferred option, the oxidative demethylation enzyme activity assayed is a human oxidative demethylation enzyme.

In embodiments of the present invention, the formaldehyde detection reagent includes 4-amino-3-penten-2-one.

Embodiments of the present invention include mixing ammonium acetate, acetyl acetone and acetic acid in a solvent to produce the formaldehyde detection reagent. The ammonium acetate added to a concentration in the range of about 0.125M-8M, inclusive, the acetyl acetone added to a concentration in the range of about 0.005M-1.6M, inclusive, and the acetic acid added to a concentration in the range of about 0.0125M-3.2M, inclusive. In preferred embodiments, the formaldehyde detection reagent so produced is not purified to remove unreacted ammonium acetate, acetyl acetone and/or acetic acid.

Method of producing a formaldehyde detection reagent are provided according to the present invention which include mixing ammonium acetate, acetyl acetone and acetic acid in a solvent, the ammonium acetate added to a concentration in the range of about 0.125M-8M, inclusive, the acetyl acetone added to a concentration in the range of about 0.005M-1.6M, inclusive, and the acetic acid added to a concentration in the range of about 0.0125M-3.2M, inclusive, to produce the formaldehyde detection reagent. Optionally, the solvent is aqueous.

Methods of screening a test agent for activity to modulate an oxidative demethylation enzyme are provided according to embodiments of the present invention which include preparing a test reaction including an oxidative demethylation enzyme, a substrate for the oxidative demethylation enzyme, a test agent and a formaldehyde detection reagent under reaction conditions which allow generation of formaldehyde by oxidative demethylation of the substrate by the enzyme in the absence of the test agent. Fluorescence is assayed in the test reaction and detected fluorescence is indicative of reaction of formaldehyde and the formaldehyde detection reagent in the test reaction. Assays according to embodiments of the present invention allow precise quantitatation of formaldehyde and therefore inventive assays allow a user to determine enzyme kinetic characteristics for each particular oxidative demethylase enzyme, for example in the presence or absence of a putative modulator.

Fluorescence detected in the test reaction is compared with fluorescence detected in a control and a difference in detected fluorescence comparing the test reaction and control is indicative of a change in activity of the oxidative demethylation enzyme in the presence of the test agent.

Optionally, a plurality of test reactions is prepared, fluorescence is detected in the plurality of test reactions and the detected fluorescence in the plurality of test reactions is compared with one or more controls to determine whether a test agent is a modulator of demethylating activity of an oxidative demethylation enzyme.

Methods of detecting formaldehyde are provided according to embodiments of the present invention which include reacting a formaldehyde detection reagent and a sample to be tested for the presence of formaldehyde, thereby generating a test sample; and detecting fluorescence in the test sample. In preferred embodiments the sample is a liquid sample and the formaldehyde detection reagent is a liquid.

Methods of detecting formaldehyde are provided according to embodiments of the present invention which include mixing ammonium acetate, acetyl acetone and acetic acid in a solvent, the ammonium acetate added to a concentration in the range of about 0.125M-8M, inclusive, the acetyl acetone added to a concentration in the range of about 0.005M-1.6M, inclusive, and the acetic acid added to a concentration in the range of about 0.0125M-3.2M, inclusive, to produce a formaldehyde detection reagent; reacting the formaldehyde detection reagent with a sample to be tested for the presence of formaldehyde, thereby generating a test sample; and detecting fluorescence in the test sample. In preferred embodiments, the formaldehyde detection reagent so produced is not purified to remove unreacted ammonium acetate, acetyl acetone and/or acetic acid prior to reaction with the sample. Thus, for example, following combination of ammonium acetate, acetyl acetone and acetic acid in a solvent to produce a solution which is a formaldehyde detection reagent, also called Luminos reagent herein, in preferred embodiments the formaldehyde detection reagent is used "as is" without purification, addition, or removal of material from the solution. Optionally, in preferred embodiments, a preservative, such as an antimicrobial, is added to the Luminos reagent and the formaldehyde detection reagent including the preservative is used "as is" without purification, addition, or removal of material from the solution.

Kits for detecting liquid phase formaldehyde are provided according to embodiments of the present invention which include a formaldehyde detection reagent, the reagent produced by mixing ammonium acetate, acetyl acetone and acetic acid in a solvent, the ammonium acetate added to a concentration in the range of about 0.125M-8M, inclusive, the acetyl acetone added to a concentration in the range of about 0.005M-1.6M, inclusive, and the acetic acid added to a concentration in the range of about 0.0125M-3.2M, inclusive. In preferred embodiments, the formaldehyde detection reagent so produced is not purified to remove unreacted ammonium acetate, acetyl acetone and/or acetic acid prior to reaction with the sample.

DETAILED DESCRIPTION OF THE PREFERRED EMBODIMENTS

Methods for measuring enzyme-mediated oxidative demethylation activity are provided according to embodiments of the present invention. Assays of the present invention allow for quantitative and direct measurement of the oxidative demethylase enzyme activity reaction by-product formaldehyde while limiting interference due to excitation or emission artifacts. Assays of the present invention find utility, for example, in screening assays for drugs which affect enzyme-mediated oxidative demethylation reactions.

Methods of assaying oxidative demethylation of a substrate by an oxidative demethylation enzyme are provided according to embodiments of the present invention which include combining an oxidative demethylation enzyme, a substrate for the oxidative demethylation enzyme and a formaldehyde detection reagent. Fluorescence from a reaction product of formaldehyde and the formaldehyde detection reagent is then detected, thereby assaying for enzyme activity since the formaldehyde is generated by oxidative demethylation of the substrate by the enzyme.

Enzyme activity assays of the present invention are readily adapted to high-throughput screening, such as screening for oxidative demethylase modulators.

The terms "oxidative demethylases" and "oxidative demethylation enzymes" and the singular form of these terms are used interchangeably herein to refer to enzymes which catalyze removal of at least one methyl group from a protein, a peptide, a nucleic acid, and/or a biological small molecule. Examples of formaldehyde-producing oxidative demethylase enzymes include, but are not limited to, DNA demethylases, histone demethylases (HDMs), and cytochrome P450 enzymes that demethylate drugs and other xenobiotic compounds.

Histone demethylases include lysine-specific and arginine-specific histone demethylases.

Lysine-specific HDMs were first discovered in 2004 and are currently among the most actively studied formaldehyde-producing oxidative demethylase enzymes. HDMs catalyze the site-specific demethylation of methyllysine residues in histones to dynamically regulate chromatin structure, gene expression, and potentially other genomic functions. Histone demethylases are described, for example, in F. Tamanoi and S. Clarke, The Enzymes, Volume 24: Protein Methyltransferases, Academic Press; 1st ed., 2006.

At present, there are two known classes of lysine-specific HDMs: the flavin adenine nucleotide (FAD)-dependent Lysine Specific Demethylase 1 (LSD1) family, such as described in Y. Shi et al. Cell, 119: 941-953, 2004, and the Fe(II)-dependent Jumonji C (JmjC) family, such as described in Y. Tsukada, et al., Nature, 439:811-816, 2006. Although the LSD1 and JmjC HDMs employ different cofactors and catalytic mechanisms, both produce formaldehyde as a byproduct of the demethylation reaction.

Figure 1A:
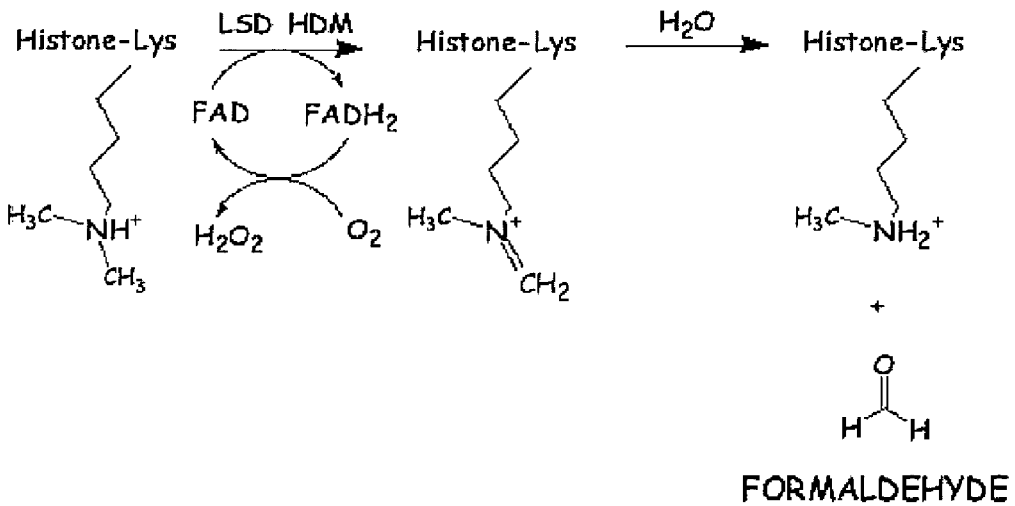
FIG. 1A is a diagram showing a reaction scheme of an (FAD)-dependent Lysine Specific Demethylase 1 (LSD1) histone demethylase.

FIG. 1 illustrates schematic chemical mechanisms of lysine demethylation. In FIG. 1A flavin adenine dinucleotide (FAD) dependent demethylation of mono- and dimethyllysines by LSD1 is shown. The oxidation of the methyl ϵ-ammonium group forms an imine intermediate that subsequently hydrolyzes to yield the demethylated lysine and a molecule of formaldehyde.

Figure 1B:
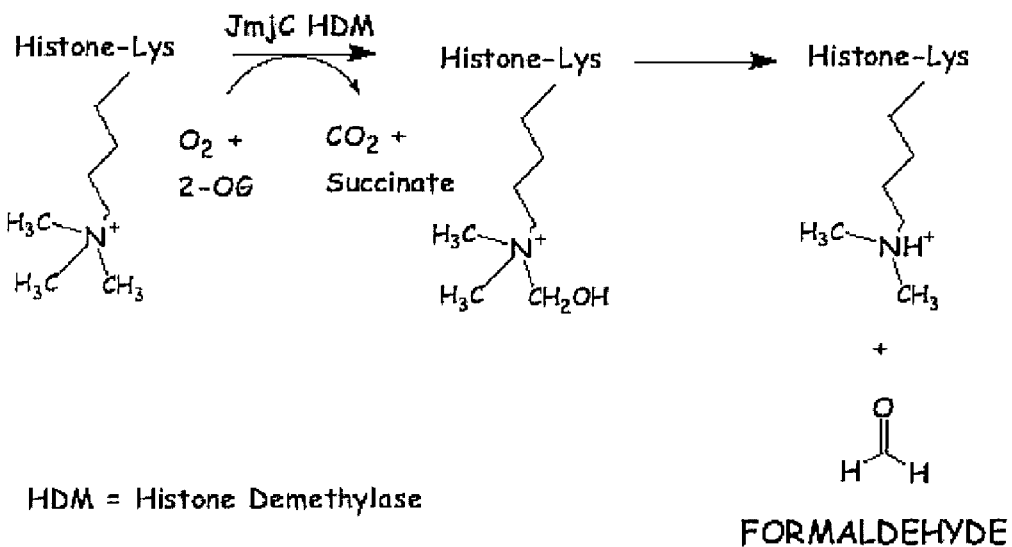
FIG. 1B is a diagram showing a reaction scheme of an Fe(II)-dependent Jumonji C (JmjC) histone demethylase.

In FIG. 1B Fe(II)-dependent demethylation of mono-, di-, and trimethyllysines by JmjC HDMs is illustrated. Using the cofactors $O_2$ and alpha-ketoglutarate (2-OG), JmjC enzymes catalyze the hydroxylation of a lysine methyl group via a radical-based mechanism, forming the products succinate and $CO_2$. The hydroxyl-methyl ammonium hemiaminal intermediate subsequently decomposes to yield the demethylated lysine and formaldehyde.

Examples of lysine-specific HDMs include LSD1 (H3K4-specific) as described in Shi Y, Lan F, Matson C, Mulligan P, Whetstine J R, Cole P A, Casero R A, Shi Y. (2004) Histone demethylation mediated by the nuclear amine oxidase homolog LSD1. Cell. 119: 941-53; JHDM1a (H3K36me1/2-specific) as described in Tsukada Y, Fang J, Erdjument-Bromage H, Warren M E, Borchers C H, Tempst P, Zhang Y. (2006) Histone demethylation by a family of JmjC domain-containing proteins. Nature. 439: 811-6; JHDM2a (H3K9me1/2-specific) as described in Yamane K, Toumazou C, Tsukada Y, Erdjument-Bromage H, Tempst P, Wong J, Zhang Y. (2006) JHDM2A, a JmjC-containing H3K9 demethylase, facilitates transcription activation by androgen receptor. Cell. 125:483-95; JHDM3A/JMJD2A Family (H3K9me2/3 and H3K36me2/3-specific) as described in Klose R J, Yamane K, Bae Y, Zhang D, Erdjument-Bromage H, Tempst P, Wong J, Zhang Y. (2006) The transcriptional repressor JHDM3A demethylates trimethyl histone H3 lysine 9 and lysine 36. Nature. 442: 312-6; Whetstine J R, Nottke A, Lan F, Huarte M, Smolikov S, Chen Z, Spooner E, Li E, Zhang G, Colaiacovo M, Shi Y. (2006) Reversal of histone lysine trimethylation by the JMJD2 family of histone demethylases. Cell. 125: 467-81; Fodor B D, Kubicek S, Yonezawa M, O'Sullivan R J, Sengupta R, Perez-Burgos L, Opravil S, Mechtler K, Schotta G, Jenuwein T. (2006) Jmjd2b antagonizes H3K9 trimethylation at pericentric heterochromatin in mammalian cells. Genes Dev. 20: 1557-62; Cloos P A, Christensen J, Agger K, Maiolica A, Rappsilber J, Antal T, Hansen K H, Helin K. (2006) The putative oncogene GASC1 demethylates tri- and dimethylated lysine 9 on histone H3. Nature. 442: 307-11; JARID1 Family (H3K4me2/3-specific) as described in Klose R J, Yan Q, Tothova Z, Yamane K, Erdjument-Bromage H, Tempst P, Gilliland D G, Zhang Y, Kaelin W G Jr. (2007) The retinoblastoma binding protein RBP2 is an H3K4 demethylase. Cell. 128: 889-900; Christensen J, Agger K, Cloos P A, Pasini D, Rose S, Sennels L, Rappsilber J, Hansen K H, Salcini A E, Helin K. (2007) RBP2 belongs to a family of demethylases, specific for tri- and dimethylated lysine 4 on histone 3. Cell. 128: 1063-76; Iwase S, Lan F, Bayliss P, de la Torre-Ubieta L, Huarte M, Qi H H, Whetstine J R, Bonni A, Roberts T M, Shi Y. (2007) The X-linked mental retardation gene SMCX/JARID1C defines a family of histone H3 lysine 4 demethylases. Cell. 128: 1077-88; Lee M G, Norman J, Shilatifard A, Shiekhattar R. (2007) Physical and functional association of a trimethyl H3K4 demethylase and Ring6a/MBLR, a polycomb-like protein. Cell. 128: 877-87; Yamane K, Tateishi K, Klose R J, Fang J, Fabrizio L A, Erdjument-Bromage H, Taylor-Papadimitriou J, Tempst P, Zhang Y. (2007) PLU-1 is an H3K4 demethylase involved in transcriptional repression and breast cancer cell proliferation. Mol Cell. 25: 801-12; UTX-JMJD3 (H3K27me2/3-specific) as described in De Santa F, Totaro M G, Prosperini E, Notarbartolo S, Testa G, Natoli G. (2007) The histone H3 lysine-27 demethylase Jmjd3 links inflammation to inhibition of polycomb-mediated gene silencing. Cell. 130: 1083-94; Agger K, Clobs P A, Christensen J, Pasini D, Rose S, Rappsilber J, Issaeva I, Canaani E, Salcini A E, Helin K. (2007) UTX and JMJD3 are histone H3K27 demethylases involved in HOX gene regulation and development. Nature. 449: 731-4; and Lan F, Bayliss P E, Rinn J L, Whetstine J R, Wang J K, Chen S, Iwase S, Alpatov R, Issaeva I, Canaani E, Roberts T M, Chang H Y, Shi Y. (2007) A histone H3 lysine 27 demethylase regulates animal posterior development. Nature. 449: 689-94.

Examples of arginine-specific histone demethylases include JMJD6 as described in B. Chang et al., Science, 2007, 318:444-447. JMJD6 demethylates H3R2me2 and H4R3me2.

DNA demethylases catalyze the removal of methyl groups from methylated nucleotides, such as DNA and RNA nucleotides, through oxidation to form formaldehyde as a byproduct. Examples of DNA demethylases include the *Escherichia coli* AlkB protein and human homologs, such as described in Wei, Y. F. et al., Nucleic Acids Res., 24 (5):931-937, 1996; Westbye, M. P. et al., J. Biol. Chem., 283(36):25046-25056, 2008; Aas, P. A. et al., Nature, 421(6925): 859-863, 2003; and Kondo, H. et al., J. Biol. Chem., 261(33):15772-15777, 1986.

Cytochrome P450 oxidative demethylases demethylate drugs and other xenobiotic compounds, producing formaldehyde as a byproduct. Examples of P450 oxidative demethylases include 14α-methyl demethylase cytochrome P450, such as described in Trzaskos et al., J. Biol. Chem., 261: 14651-14657, 1986 and enzymes described in Hollenberg, P. F., FASEB J., 6:686-694, 1992 and McLean, K. J., et al., Biochem. Soc. Trans, 34:1178-1182, 2006.

Assays of the present invention can be used with oxidative demethylases from any species, including but not limited to, humans, non-human primates, cows, horses, sheep, pigs, dogs, cats, birds, rodents, fish, amphibians, reptiles, viruses, bacteria, plants and fungi. In preferred embodiments, assays of the present invention include one or more human oxidative demethylases.

A sample containing one or more oxidative demethylases can be assayed for oxidative demethylase activity according to embodiments of the present invention. A sample can be a sample obtained from a subject, such as a bodily fluid, cell or tissue sample illustratively including blood, plasma, serum, urine, saliva, ascites, cerebrospinal fluid, cerebroventricular fluid, pleural fluids, pulmonary and bronchial lavage samples, mucous, sweat, tears, semen, bladder wash samples, amniotic fluid, lymph, peritoneal fluid, synovial fluid, bone marrow aspirate, tumor cells or tissue, organ cells and tissue, such as biopsy material.

Oxidative demethylases can be obtained commercially or prepared for inclusion in an inventive assay by any of various methods, such as by recombinant molecular methodology using well-known techniques.

The terms "oxidative demethylases" and "oxidative demethylation enzymes" include amino acid sequence variants of wild-type oxidative demethylases. Amino acid sequence variants can have one or more amino acid substitutions, additions or deletions. Amino acid variants of oxidative demethylases can have a single amino acid difference compared to a wild-type oxidative demethylase or may have more than one amino acid difference. In general, amino acid sequence variants have about at least 70%, 80%, 85%, 90%, 91%, 92%, 93%, 94%, 95%, 96%, 97,%, 98%, 99% or more amino acid sequence identity with a reference wild-type oxidative demethylase.

Percent identity is typically determined by comparison of amino acid sequences. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

Amino acid sequence variants of wild-type oxidative demethylases can be prepared by recombinant molecular techniques, such as site-specific mutagenesis or PCR-mediated mutagenesis to produce a nucleic acid encoding an amino acid sequence variant of a wild-type oxidative demethylase. The mutant nucleic acid can then be expressed, for example in recombinant cells in culture, to produce an amino acid sequence variant of a wild-type oxidative demethylase.

Substrates for oxidative demethylation enzymes can be naturally occurring or synthetic protein, peptide, nucleic acid and/or small organic molecule substrates. Substrates for particular oxidative demethylation enzymes are known or can be easily ascertained by one of ordinary skill in the art through routine experimentation.

Examples of naturally occurring protein substrates for histone demethylases are free and nucleosomal histones. Histones can be isolated from cell nuclei, for example as described in Kornberg, R. D., et al., Methods Enzymol., 170: 3-14 or obtained commercially from various sources such as Sigma-Aldrich, Inc.

Synthetic peptides can be used as substrates for oxidative demethylation enzymes. In particular embodiments, peptides including at least one methylated lysine are substrates for lysine demethylases. For example, a synthetic peptide, H$_2$N-ARTKQTARK(tri-methyl)STGGKA-amide (SEQ ID NO. 1), also called H3K9me3, is a substrate for human JmjD2a. Residues 1-21 from the N-terminal tail of human histone H3, dimethylated on the side-chain, ε-amino function, of lysine-4: ARTK (Me2) QTARKSTGGKAPRKQLA-NH$_2$ (SEQ ID NO. 2), is a substrate for histone lysine demethylases.

Additional substrates for particular oxidative demethylases are known in the art and can be used in assays and included in kits according to embodiments of the present invention. Non-limiting examples of such substrates are described in Tian, X. et al., Acta Biochimica et Biophysica Sinica, 39(2):81-88, 2007.

Reaction Conditions

In particular embodiments, reaction conditions for oxidative demethylation enzyme activity assays of the present invention include, but are not limited to, reaction conditions which approximate physiological conditions with respect to one or more of: temperature, pH and ionic strength. Specific reaction conditions depend on the identity of the reaction components and determination of suitable reaction conditions is performed without undue experimentation by one of ordinary skill in the art.

Cofactors or other reagents suitable for use in assays of the present invention can be included in test and control reactions. Enzyme cofactors included depend on the identity of the particular oxidative demethylation enzyme assayed and such cofactors are known or can be determined by one of skill in the art employing routine experimentation. For example Fe(II), O$_2$ and alpha-ketoglutarate (2-OG) are cofactors for JmjC HDMs. FAD is a cofactor for LSD1 HDMs.

In specific embodiments, methods of the present invention include a fluorescent assay that detects formaldehyde via its reaction with a formaldehyde detection reagent.

In embodiments of the present invention, 4-amino-3-penten-2-one, also known as Fluoral P, is a formaldehyde detection reagent included in an oxidative demethylase assay. Fluoral P reacts with formaldehyde to produce a fluorescent product as shown in Scheme 1.

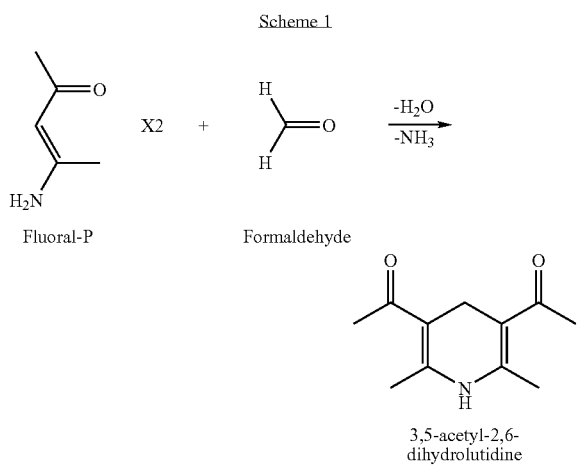

Scheme 1

Fluoral-P    Formaldehyde 3,5-acetyl-2,6-dihydrolutidine

In particular embodiments, a formaldehyde detection reagent termed the "Luminos reagent" herein, is used in assays of the present invention which is produced by mixing ammonium acetate, acetyl acetone and acetic acid in a solvent. Any aqueous or non-aqueous solvent can be used in which the ammonium acetate, acetyl acetone and acetic acid are soluble. In preferred embodiments, the solvent is water.

In embodiments of the present invention, Luminos reagent is produced by generating a mixture in which: ammonium acetate has a final concentration in the range of about 0.125M-8M, inclusive, acetyl acetone has a final concentration in the range of about 0.005M-1.6M, inclusive, and acetic acid has a final concentration in the range of about 0.0125M-3.2M, inclusive. In preferred embodiments, Luminos reagent is produced by generating a mixture in which: ammonium acetate has a final concentration in the range of about 0.25M-6M, inclusive, acetyl acetone has a final concentration in the range of about 0.01M-0.5M, inclusive, and acetic acid has a final concentration in the range of about 0.025M-1.0M, inclusive. In further preferred embodiments, Luminos reagent is produced by generating a mixture in which: ammonium acetate has a final concentration in the range of about 0.75M-4M, inclusive, acetyl acetone has a final concentration in the range of about 0.015M-0.16M, inclusive, and acetic acid has a final concentration in the range of about 0.025M-0.1M, inclusive. In a further preferred embodiment, Luminos reagent is prepared as a solution of about 1M ammonium acetate, about 0.02M acetylacetone and about 0.05M acetic acid.

The Luminos reagent reacts with formaldehyde to form an adduct that exhibits an emission maximum at 510 nm when excited between 340 to 460 nm. The Luminos reagent is a highly sensitive formaldehyde detection reagent and can detect formaldehyde concentrations of about 100 nanomolar or lower as well as higher concentrations.

Without wishing to be bound by theory, it is believed that 4-amino-3-penten-2-one is formed in the Luminos reagent. One or more additional species reactive with formaldehyde to form a fluorescent adduct may also be present. In contrast to commercially available formulations, the 4-amino-3-penten-2-one in the Luminos reagent is not separated from unreacted materials and unexpectedly, the fluorescent signal:noise ratio produced in assays of the present invention using the Luminos reagent is higher than that produced using a comparable amount of purified 4-amino-3-penten-2-one. Thus, when an amount of Luminos reagent prepared as described in Example 1 and an amount of 95% pure 4-amino-3-penten-2-one obtained commercially from Maybridge International are adjusted to have identical OD at 300 nm, the Luminos reagent yields a higher signal:noise ratio in formaldehyde detection assays described herein.

Thus, for example, following combination of ammonium acetate, acetyl acetone and acetic acid in a solvent to produce a solution which is a formaldehyde detection reagent, also called Luminos reagent herein, in preferred embodiments the formaldehyde detection reagent is used "as is" without purification, addition, or removal of material from the solution. Optionally, in preferred embodiments, a preservative, such as an antimicrobial, is added to the Luminos reagent and the formaldehyde detection reagent including the preservative is used "as is" without purification, addition, or removal of material from the solution.

Optionally, a preservative is present in the formaldehyde detection reagent. For example, a biocidal agent is present in amounts suitable to inhibit microbial growth in the formaldehyde detection reagent. An exemplary preservative is sodium azide.

An amount of a formaldehyde detection reagent, such as 4-amino-3-penten-2-one and Luminos reagent included in an assay according to embodiments of the present invention depends on the amount of formaldehyde produced in an oxidative demethylase reaction and appropriate amounts for a particular assay can be determined by one of skill in the art using routine experimentation. Generally, purified 4-amino-3-penten-2-one from 0.1 to 10 mg/mL can be used in an assay according to embodiments of the present invention. Similarly, various volumes of Luminos reagent can be used in conjunction with an assay according to embodiments of the present invention. For levels of formaldehyde between 200 and 1 µM a ratio of 2 parts sample to 1 part Luminos reagent could be used. For higher formaldehyde concentrations, lower ratios of Luminos reagent can be used. For lower formaldehyde concentrations higher ratios may give better sensitivity.

Assays may be carried out on cuvettes, microtiter plates, or other vessels capable of being used for fluorescent measurements with volumes ranging from several milliliters down to nanoliter volumes.

Assays according to embodiments of the present invention include detection of a fluorescent adduct of 4-amino-3-penten-2-one and formaldehyde having an emission maximum at 510 nm when excited between 340 to 460 nm. Fluorescence detection is accomplished using any suitable fluorescence detection methods and apparatus. Fluorescence detection methods and fluorometric apparatus are well-known, for example, as described in J. R. Lakowicz, Principles of Fluorescence Spectroscopy, Springer, 3rd ed., 2006.

Methods of screening a test agent for activity to modulate an oxidative demethylation enzyme are provided according to embodiments of the present invention which include preparing a test reaction including an oxidative demethylation enzyme, a substrate for the oxidative demethylation enzyme, a test agent and a formaldehyde detection reagent under conditions which allow generation of formaldehyde by oxidative demethylation of the substrate by the enzyme in the absence of the test agent. The test reaction is assayed for fluorescence indicative of formaldehyde in the test reaction. Fluorescence detected in the test reaction is compared with a control and differences in detected fluorescence in the test reaction and control are indicative of a change in activity of the oxidative demethylation enzyme in the presence of the test agent.

Methods of detecting formaldehyde are provided according to embodiments of the present invention which include combining ammonium acetate, acetyl acetone and acetic acid to produce a formaldehyde detection reagent, a Luminos reagent, as described herein. The formaldehyde detection reagent is incubated with a sample to be tested for the presence of formaldehyde, thereby generating a test sample. The test sample is assayed for fluorescence, detected fluorescence indicative of the presence of formaldehyde in the test sample.

Methods of quantifying the absolute amount of formaldehyde in a sample according to embodiments of the present invention optionally include generation of a standard or standard curve using known amounts of formaldehyde and comparing fluorescence generated in the sample with the fluorescence generated using the standard or standards to ascertain the amount of formaldehyde in the sample.

In embodiments of the present invention, formaldehyde is detected in a sample using a Luminos reagent as described herein. The sample can be a sample obtained from a subject, such as a bodily fluid, cell or tissue sample. In preferred embodiments, the sample is a liquid sample, such as blood, plasma, serum, urine, saliva, ascites, cerebrospinal fluid, cerebroventricular fluid, pleural fluids, pulmonary and bronchial lavage samples, mucous, sweat, tears, semen, bladder wash samples, amniotic fluid, lymph, peritoneal fluid and synovial fluid.

A "test agent" is any molecule, such as a protein, peptide, small organic molecule, polysaccharide, oligosaccharide, oligonucleotide or polynucleotide to be tested for activity to modulate activity of an oxidative demethylation enzyme in an assay according to embodiments of the present invention.

Test agents can be obtained from any of numerous sources for use in methods of the present invention. For example, libraries of natural or synthetic organic compounds are available or readily produced using well-known isolation and/or synthetic techniques. Generation of organic compounds as test agents, including small organic molecules and biomolecules, using directed or random synthesis is readily accomplished using conventional technologies such as chemical, biochemical and/or recombinant technologies. Known pharmacological substances can be used as test agents in methods of the present invention and such known pharmacological substances can be modified to produce additional test agents using conventional technologies such as chemical, biochemical and/or recombinant technologies, including, for example, acylation, alkylation, amidification and/or esterification.

Proteins and peptides used as test agents may include naturally occurring amino acids linked by peptide bonds and/or may include synthetic peptidomimetic structures. In particular embodiments, peptides have from about 2-about 30 amino acids or more. Such proteins and peptides may be derived from any source, illustratively including mammalian, avian, reptilian, amphibian, bacterial and viral. Human proteins and peptides are particularly preferred as test agents. Proteins and peptides can be from any source, such as naturally occurring biomolecules, digested or chemically cleaved fragments of naturally occurring biomolecules or directed or randomly synthesized proteins and peptides.

Nucleic acid test agents can be oligonucleotides or polynucleotides in particular embodiments. Oligonucleotides have from about 2-about 30 covalently linked nucleotides and/or any of various nucleotide analogs. Oligonucleotides and polynucleotides used as test agents can be from any source, such as naturally occurring biomolecules, digested or chemically cleaved fragments of naturally occurring biomolecules or directed or randomly synthesized oligonucleotides and polynucleotides. Such oligonucleotides and polynucleotides may be derived from any source, illustratively including mammalian, avian, reptilian, amphibian, bacterial and viral.

Carbohydrate test agents can be oligosaccharides or polysaccharides in particular embodiments. Oligonucleotides have from about 2-about 10 covalently linked sugars and/or any of various sugar analogs. Oligosaccharides and polysaccharides used as test agents can be from any source, such as naturally occurring biomolecules, digested or chemically cleaved fragments of naturally occurring biomolecules or directed or randomly synthesized oligosaccharides or polysaccharides. Such oligosaccharides or polysaccharides may be derived from any source, illustratively including mammalian, avian, reptilian, amphibian, bacterial and viral.

A wide variety of small molecule organic compound test agents are available from commercial source or can be readily produced, for example, as described in G. Fassina and S. Miertus (Eds.), Combinatorial Chemistry and Technologies: Methods and Applications, 2nd Ed., CRC Press, 2005.

One of skill in the art will recognize that test agents can be combinations of proteins, peptides, small organic molecules, polysaccharides, oligosaccharides, oligonucleotides and/or polynucleotides, such as glycoproteins.

Control Reactions

Results of assays according to embodiments of the present invention are compared to a control or standard in order to assess the results, such as the activity level of an enzyme and/or the ability of a test agent to modulate activity of an enzyme. For example, a negative control reaction is prepared according to particular embodiments which excludes a component of a test reaction, such as a cofactor necessary for enzyme activity and/or a substrate for the enzyme. A positive control reaction can be performed which includes all reaction components necessary to produce formaldehyde as a reaction product of oxidative demethylation, such as an oxidative demethylase, a substrate for the oxidative demethylase and one or more cofactors. Alternative positive controls include a sample containing formaldehyde, such as a known amount of formaldehyde. In particular embodiments, a plurality of assays is performed in parallel using a range of amounts of formaldehyde.

An inhibitor of an oxidative demethylase can be included in an assay according to embodiments of the present invention. An inhibitor is incubated with a sample putatively containing an oxidative demethylase and/or in a reaction containing a known amount of an oxidative demethylase, for example, as an assay control.

Because LSD1 belongs to the family of flavin adenine dinucleotide (FAD)-dependent amine oxidases, certain inhibitors of monoamine oxidases (MAOs), including the clinically used antidepressant trans-2-phenylcyclopropylamine (PCPA; tranylcypromine; Parnate), inhibit LSD1 and can be included in an assay of the present invention in a control reaction.

A difference between a result of a test reaction and a result of a control reaction is generally considered significant when the difference is greater than the experimental error associated with the assay. Assessment of significance of differences in assays can be performed using conventional statistical techniques.

High Throughput Screening

Methods for screening test agents for activity to modulate oxidative demethylase activity are provided according to embodiments of the present invention. In particular embodiments, methods according to the present invention are high throughput screening methods. High throughput screening methods typically allow for assay of many test agents and samples, often using automation.

High throughput screening methods can incorporate high throughput screening systems which automate some or all aspects of the assay procedure, such as automated reagent dispensing, reaction timing, heating or cooling, mixing and reading assay output. High throughput systems are commercially available, for example from Beckman Coulter, Inc.

Assays according to embodiments of the present invention can be performed in any of a variety of reaction vessel formats, illustratively including, but not limited to, microfuge tubes, microtiter plates such as plates having 96, 384, 1536 or another number of wells or similar supports containing depressions for receiving reaction components or a prepared reaction.

In one example, test agents are assayed in parallel for enzyme modulatory activity individually or in mixtures by placing assay components, including an oxidative demethylase, an oxidative demethylase substrate, one or more cofactors and a formaldehyde detection reagent, in reaction vessels, and the fluorescence of each reaction vessel detected using an appropriate detection device. Test agents which modulate the oxidative demethylase are identified by an increase or decrease in produced formaldehyde as detected by increased or decreased fluorescence compared to a control reaction performed in absence of the test agent.

In embodiments of assays of the present invention, formaldehyde production is measured at two or more time points in order to acquire kinetic information relating to enzyme activity. Thus, for example, fluorescence is detected in a reaction at two or more time points.

Kits

Kits for use in performing assays according to embodiments of the present invention are provided which include reaction components necessary for detecting formaldehyde in a liquid sample. In particular embodiments, kits for use in performing assays according to embodiments of the present invention are provided which include a formaldehyde detection reagent which forms a fluorescent product in the presence of formaldehyde. The formaldehyde detection reagent preferably includes 4-amino-3-penten-2-one. In a preferred option, the formaldehyde detection reagent including 4-amino-3-penten-2-one is a Luminos reagent produced by generating a mixture in which: ammonium acetate has a final concentration in the range of about 0.125M-8M, inclusive, acetyl acetone has a final concentration in the range of about 0.005M-1.6M, inclusive, and acetic acid has a final concentration in the range of about 0.0125M-3.2M, inclusive. In preferred embodiments, Luminos reagent included in an inventive kit is produced by generating a mixture in which: ammonium acetate has a final concentration in the range of about 0.25M-6M, inclusive, acetyl acetone has a final concentration in the range of about 0.01M-0.5M, inclusive, and acetic acid has a final concentration in the range of about 0.025M-1.0M, inclusive. In further preferred embodiments, Luminos reagent included in an inventive kit is produced by generating a mixture in which: ammonium acetate has a final concentration in the range of about 0.75M-4M, inclusive, acetyl acetone has a final concentration in the range of about 0.015M-0.16M, inclusive, and acetic acid has a final concentration in the range of about 0.025M-0.1M, inclusive. In a further preferred embodiment, Luminos reagent included in an inventive kit is prepared as a solution of about 1M ammonium acetate, about 0.02M acetylacetone and about 0.05M acetic acid.

In a further option, one or more oxidative demethylase substrates, cofactors, buffers and/or diluents is included in a kit according to embodiments of the present invention.

In one embodiment, a kit of the present invention is an LSD-1 assay kit. Optionally, an LSD-1 kit according to embodiments of the present invention includes LSD-1 or a fragment thereof, such as the N-terminal truncation of human LSD-1 having residues 151-852, Genbank Accession # NM_015013.

An LSD-1 substrate is optionally included in a kit for assay of LSD-1. For example, mono- or dimethylated histone H3, lysine residue 4 (H3,K4) or histone H3, lysine 9 (H3K9) is included in embodiments of inventive kits.

FAD is optionally included in a kit for assay of LSD-1.

In a further embodiment, a kit of the present invention is an Jumonji Type Histone Demethylase assay kit. Optionally, an Jumonji Type Histone Demethylase kit according to embodiments of the present invention includes a Jumonji-type histone demethylase or a fragment thereof such as the catalytic domain, residues 1-350, of the human Jumonji-type histone demethylase JMJD2A.

A Jumonji-type histone demethylase substrate is optionally included in a kit for assay of a Jumonji-type histone demethylase. For example, H3K9me3 substrate peptide is included in embodiments of inventive kits.

A cofactor of a Jumonji-type histone demethylase is optionally included in a Jumonji-type histone demethylase assay kit.

Embodiments of inventive compositions and methods are illustrated in the following examples. These examples are provided for illustrative purposes and are not considered limitations on the scope of inventive compositions and methods.

EXAMPLES

Example 1

Preparation of Luminos Reagent for Formaldehyde Detection

A "Luminos reagent" for formaldehyde detection used in methods according to the present invention is prepared by mixing ammonium acetate, acetyl acetone and acetic acid with a solvent. The product of this mixing is termed the "Luminos reagent" herein.

In this example, to make the Luminos reagent, a solution having a final concentration of 1M ammonium acetate, 0.05 M glacial acetic acid, 0.02 M acetylacetone and 0.90% sodium azide is generated. To make a 1 mL amount of the Luminos reagent, 77.08 mg of ammonium acetate is mixed with 0.70 mLs of deionized water. Then, 2.874 µLs of 17.4 M glacial acetic acid is slowly added to the ammonium acetate solution and stirred until mixed. Acetylacetone, 2.053 µLs, is added to the ammonium acetate/acetic acid solution with vigorous stirring until mixed. Sodium azide, 0.90 mg, is added with further stirring and the mixture is brought to a final volume of 1 milliliter with deionized water and mixed thoroughly. The Luminos reagent is stable at 4° C. for nine months or more and at −20° C. for greater than two years.

Using pure formaldehyde as a standard, the reagent for formaldehyde detection used in methods of the present invention has a range between 200 and 3.125 µM formaldehyde. In sensitivity studies the reagent measures below 1 µM formaldehyde in water, particularly 100 nanomolar and below. Twenty replicates of the zero standard, water, gave an average reading of 1,706.4±96.1 FLU. Twenty replicates of the 3.125 µM formaldehyde standard gave an average reading of 2,481.2±134.3 FLU. Therefore the sensitivity of detection, as measured at 2 standard deviations above the zero standard (95% confidence limits), is calculated as 0.775 µM. [Delta signal between 0 and 3.125 µM was 774.8 FLU and 2 standard deviations is 2×96.1=192.2 giving the sensitivity as (2 SD signal/Delta signal)×delta formaldehyde].

A direct comparison of purified Fluoral P, 4-amino-3-penten-2-one, obtained from Maybridge Ltd, Cambridge, UK and the Luminos reagent for formaldehyde detection used in methods of the present invention provides distinct results. Both reagents are dissolved in identical buffers, 1M ammonium acetate, 0.05M acetic acid, pH 6, and identical formaldehyde standards are used in the comparison. The purified Fluoral P in the presence of a 200 µM formaldehyde standard gives a mean of 46000 FLU and the same reagent in the presence of a zero (water) standard gives 4000 FLU for a signal-to-noise ratio of 11. The Luminos reagent in the presence of a 200 µM formaldehyde standard gives a mean of over 44000 FLU and gives a zero of 1400 FLU under the same conditions and a signal to noise for the 200 µM formaldehyde standard of 32.

Example 2

Assay of Jumonji Type Histone Demethylase Activity

A series of demethylase assays with Luminos reagent are performed. These assays are conducted with recombinantly produced catalytic domain, residues 1-350, of the human histone demethylase JMJD2A that demethylates the trimethylated forms of Lys9 and Lys36 in histone H3.

Residues 1-350, of the human histone demethylase JMJD2A (SEQ ID NO. 3):

MASESETLNPSARIMTFYPTMEEFRNFSRYIAYIESQGAHRAGLAKVVPP

KEWKPRASYDDIDDLVIPAPIQQLVTGQSGLFTQYNIQKKAMTVREFRKI

ANSDKYCTPRYSEFEELERKYWKNLTFNPPIYGADVNGTLYEKHVDEWNI

GRLRTILDLVEKESGITIEGVNTPYLYFGMWKTSFAWHTEDMDLYSINYL

HFGEPKSWYSVPPEHGKRLERLAKGFFPGSAQSCEAFLRHKMTLISPLML

KKYGIPFDKVTQEAGEFMITFPYGYHAGFNHGFNCAESTNFATRRWIEYG

KQAVLCSCRKDMVKISMDVFVRKFQPERYKLWKAGKDNTVIDHTLPTPEA

A positive control assay is performed using a 100 microliter assay cocktail of 20 mM HEPES pH 7.5, 50 mM NaCl, 1 mM Sodium Ascorbate, 0.05 mM $FeSO_4$, and 5 µM JMJD2A. The assay is initiated by the addition of the cofactor 2-oxoglutarate (2-OG, 0.5 mM) and a 15-residue histone H3 trimethylated Lys9 (H3K9me3) substrate peptide (0.3 mM, $H_2N$-ARTKQTARK(tri-methyl)STGGKA-amide) (SEQ ID NO. 1).

Three negative control reactions are performed in which 2-OG, the H3K9me3 peptide, and JMJD2A are omitted, respectively. Furthermore, two additional reactions are performed with known inhibitors of JmjC histone demethylases to demonstrate that Luminos reagent can quantify small molecule-based inhibition of these enzymes. Specifically, reactions are performed with 1.0 mM N-oxalylglycine (NOG), a competitive inhibitor of 2-OG, and desferoxamine (0.2 mM), a potent Fe(II) chelator that inhibits the oxidative reaction catalyzed by Fe(II)-dependent JmjC demethylases. These assays are initiated by the addition of 2-OG and the H3K9me3 peptide. All of the reactions are performed in triplicate at 37° C. and are quenched with the addition of 5.0 uL of 4 mM desferoxamine (final concentration=0.2 mM) after 30 minutes. Fifty microliters of the Luminos reagent solution prepared as described in Example 1 is then added to each reaction and the fluorescence is allowed to develop at 37° C. for 30 minutes. The fluorescence of the formaldehyde-Luminos reagent adduct is measured at 510 nm using an excitation wavelength of 440 nm with a Tecan Safire 2 microplate reader. The triplicate measurements from each reaction are then averaged and plotted as bar graphs with standard deviation illustrated as error bars, shown in FIG. 2.

Figure 2:
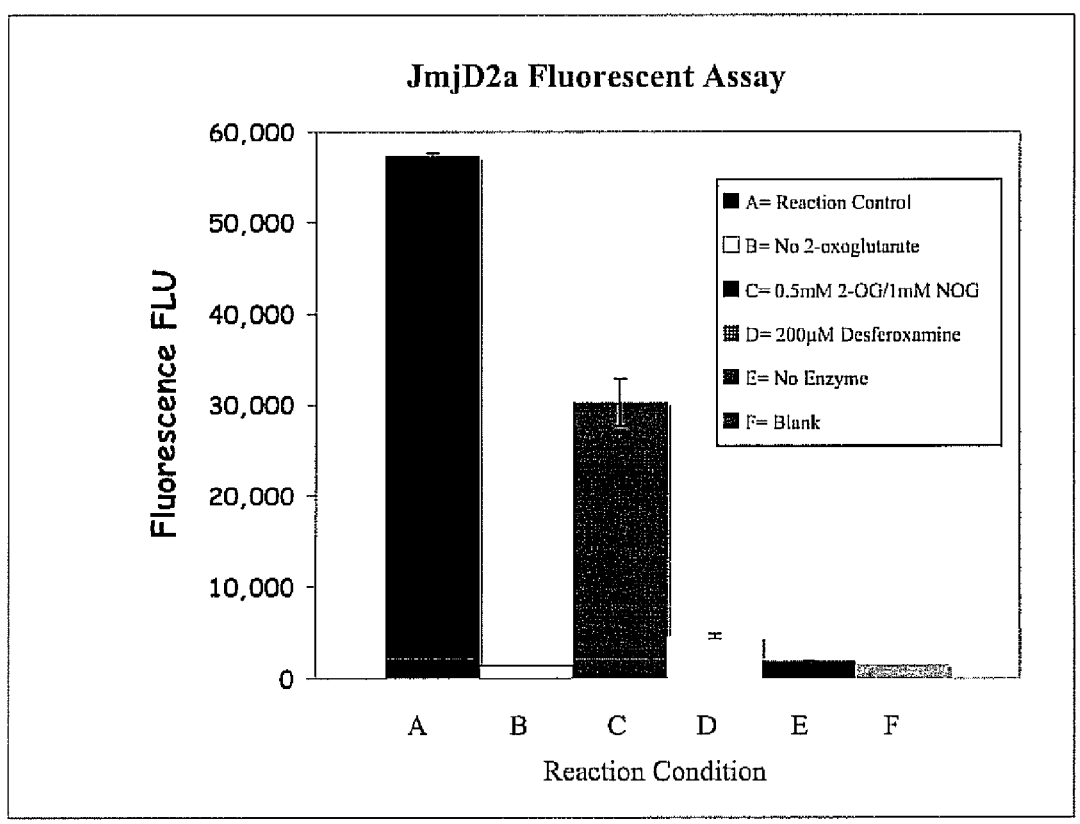
FIG. 2 is a graph showing results of an assay for oxidative demethylase activity according to embodiments of the present invention.

An analysis of the data demonstrates that the positive control assay displays strong fluorescence with Luminos reagent with low standard deviation among the three replicate assays (57,000±400 relative fluorescence units). Omission of 2-OG, the H3K9me3 peptide, or JMJD2A results in a ~30-fold reduction in the fluorescence signal. Similarly, inclusion of the demethylase inhibitors NOG and deferoxamine diminishes fluorescence two-fold and 12-fold, respectively, in comparison to the positive control assay. The modest inhibition observed with NOG (1 mM) is due to a comparable concentration of the substrate 2-OG (0.5 mM) to which NOG competes for binding to JmjC demethylases. Thus, as shown in FIG. 2, an assay of the present invention detects JmjD2a demethylase activity rapidly and sensitively.

Example 3

Assay of LSD1 Type Histone Demethylase Activity

A demethylase assay according to an embodiment of the present invention is performed using Luminos reagent to detect a direct product of the histone demethylation reaction, formaldehyde. Recombinant of LSD-1 used in the assay is the active N-terminal truncation (residues 151-852, Genbank Accession # NM_015013) of human cDNA produced recombinantly in *E. coli* (SEQ ID NO. 4):

```
LPPPPPQAPPEEENESEPEEPSGVEGAAFQSRLPHDRMTSQEAACFPDII

SGPQQTQKVFLFIRNRTLQLWLDNPKIQLTFEATLQQLEAPYNSDTVLVH

RVHSYLERHGLINFGIYKRIKPLPTKKTGKVIIIGSGVSGLAAARQLQSF

GMDVTLLEARDRVGGRVATFRKGNYVADLGAMVVTGLGGNPMAVVSKQVN

MELAKIKQKCPLYEANGQAVPKEKDEMVEQEFNRLLEATSYLSHQLDFNV

LNNKPVSLGQALEVVIQLQEKHVKDEQIEHWKKIVKTQEELKELLNKMVN

LKEKIKELHQQYKEASEVKPPRDITAEFLVKSKHRDLTALCKEYDELAET

QGKLEEKLQELEANPPSDVYLSSRDRQILDWHFANLEFANATPLSTLSLK

HWDQDDDFEFTGSHLTVRNGYSCVPVALAEGLDIKLNTAVRQVRYTASGC

EVIAVNTRSTSQTFIYKCDAVLCTLPLGVLKQQPPAVQFVPPLPEWKTSA

VQRMGFGNLNKVVLCFDRVFWDPSVNLFGHVGSTTASRGELFLFWNLYKA

PILLALVAGEAAGIMENISDDVIVGRCLAILKGIFGSSAVPQPKETVVSR

WRADPWARGSYSYVAAGSSGNDYDLMAQPITPGPSIPGAPQPIPRLFFAG

EHTIRNYPATVHGALLSGLREAGRIADQFLGAMYTLPRQATPGVPAQQSP

SM
```

LSD-1 specifically demethylates mono- or dimethylated histone H3, lysine residue 4 (H3,K4) and histone H3, lysine 9 (H3K9) to a much lesser extent. A synthetic 21-residue peptide from the N-terminal sequence of human histone H3 with dimethylation on the ε-amino function of lysine 4 (H3K4-Me2) is used as the reaction substrate. Recombinant N-terminal truncation, residues 151-852 of human LSD1 and the Histone H3 Dimethyl lysine-4 peptide substrate are available commercially from Biomol International.

The assay is performed in a black half-area microtiter plate (Costar 3686) in a total reaction volume of 100 microliters containing 25 mM potassium phosphate, pH 7.8, 5% glycerol, 50 micromolar H3K4-Me2, and 0.235 micrograms of the recombinant LSD-1.

Duplicate wells containing the 100 microliter reaction are set up to allow a comparison of simultaneous and sequential detection with purified Fluoral-P. The simultaneous reactions contained the 100 microliter reaction volume as well as 50 microliters formaldehyde detection reagent, either purified 4-amino-3-penten-2-one or Luminos reagent, while the sequential reactions contained only the 100 microliter reaction volumes. Reactions containing no enzyme or which contain no formaldehyde detection reagent are performed as controls.

The microtiter plate is incubated at 30° C. for 60 minutes then read for fluorescent signal using a BMG Labtechnologies FluoStar Galaxy in fluorescence intensity mode to detect at 510 nm (±10 nm bandwidth) wavelength with excitation wavelength at 390 nm. To evaluate the sequential format of the assay, formaldehyde detection reagent, either purified 4-amino-3-penten-2-one or Luminos reagent, is added to the sequential reaction wells (50 microliters) and the plate incubated for an additional 30 minutes at 37° C. to allow fluorescent adduct formation. The plated is read as before and the net data of all wells graphed.

Figure 3:
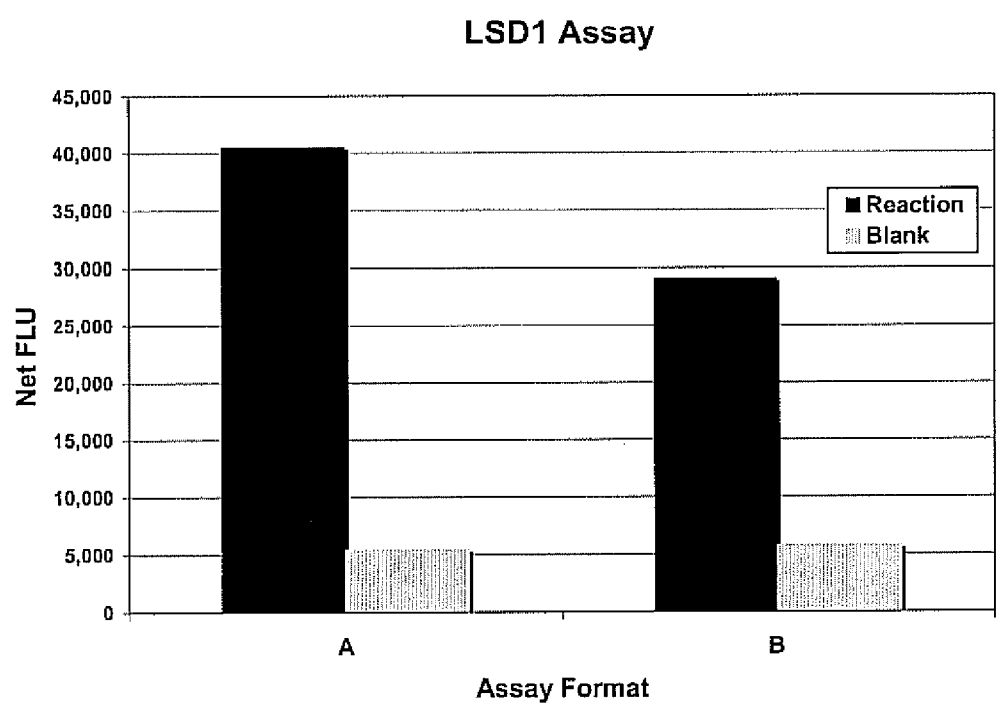
FIG. 3 is a graph showing results of an assay for oxidative demethylase activity according to embodiments of the present invention.

As noted above, in this example assay reactions are performed in 2 different assay formats. FIG. 3 is a graph showing results of both LSD1 assay types. The first LSD1 assay type is a sequential assay involved incubating the LSD1 enzyme with the dimethyl peptide in 100 μL of buffer for 60 minutes to generate formaldehyde, followed by addition of 50 μL Luminos reagent and incubating for a further 30 minutes. Results of the sequential assay are shown at A in FIG. 3. The second LSD1 assay type is a simultaneous reaction in which 100 μL of LSD1 and peptide substrate plus 50 μL of the formaldehyde detection reagent are added simultaneously and incubated for 90 minutes. Results of the simultaneous reaction are shown at B in FIG. 3.

The sequential reaction method generates a 28% greater net signal than the simultaneous reaction method. Signal generated during the sequential reaction includes not only adduct formation with already existing formaldehyde from the initial 60 minute incubation, but also from additional demethylation and adduct formation occurring during the Luminos reagent incubation.

Enzyme activity assays of the present invention can detect oxidative demethylase activity of enzymes such as LSD1 and JMJD2A with a signal to background ratio of 20:1 or greater when positive control reactions are compared with negative control assays.

Example 4

Assay of P-450 Demethylase Activity

An assay of P-450 demethylase activity is performed according to methods of the present invention. The lanosterol 14a-demethylase P-450 enzyme (P-45014DM), catalyzes the removal of a methyl group in the initial reaction in the biosynthesis of cholesterol from lanosterol. The enzyme catalyzes the oxidative demethylation of C-32 of lanosterol, forming formaldehyde as a byproduct.

The 14α-demethylase P-450 enzyme is isolated from microsomes as described in Trzaskos, J. et al., J. Biol. Chem., 261:14651-14657, 1986. The sterol substrate of the 14α-demethylase P-450 enzyme, 24,25-dihydrolanosterol, is isolated as described in Trzaskos, J. et al., J. Biol. Chem., 259: 13402-13412, 1984.

The substrate 24,25-dihydrolanosterol, is suspended in 1.33% Tyloxapol and then diluted to a final concentration of 1000 μM. The P-450 demethylation assay is performed in a black half-area microtiter plate (Costar 3686) in a final volume of 100 μL of 100 mM potassium phosphate, 0.1 mM EDTA, 0.1 mM dithiothreitol, 20% glycerol, pH 7.4, 0.02% Triton N-101, 100 pg of dilaurylphosphatidylcholine, 0.1 mM NADH, 1.0 mM NADPH, 10 mM isocitrate, 0.5 units of isocitrate dehydrogenase, 0.4 mM $MgCl_2$, 1 unit of NADPH-cytochrome-c reductase, 0.1 nmol cytochrome P-450. Incubations are started by the addition of 50 pmol of the sterol substrate. The microtiter plate is incubated at 30° C. for 60 minutes. Fifty microliters of the Luminos reagent prepared as described in Example 1 is added to appropriate wells and the plate is incubated for a further 30 minutes. The fluorescent signal is then read using a Turner Modulus in fluorescence intensity mode to detect at 510 nm (–10 nm bandwidth) wavelength with excitation wavelength at 390 nm.

Example 5

Assay of DNA Demethylase Activity

An assay is performed according to an embodiment of the present invention to detect a direct product of a DNA demethylation reaction, formaldehyde. The AlkB protein of *Escherichia coli*, and its orthologs in other organisms, catalyzes the removal of alkyl groups from methylated DNA through oxidation to form formaldehyde.

The enzymes major substrates are 1-methyladenine and 3-methylcytosine. Double-stranded methylated substrates are generated by incubating the single stranded oligonucleotides containing the methyl modifications with 1.5-fold molar excess of the unmethylated complementary oligonucleotide at 37° C. for 30 min in annealing buffer (50 mM HEPES, pH 8.0, 10 mM EDTA).

*E. coli* AlkB can be generated recombinantly as described in Roy, T. W. et al., Nucleic Acids Res., 35(21):e147.

A DNA demethylase assay in this example is performed in a black half-area microtiter plate (Costar 3686) in a total reaction volume of 100 microliters containing 20 mM HEPES, pH 8, 200 mM a-ketoglutarate, 2 mM L-ascorbic acid, 20 mM $Fe(NH4)_2(SO_4)_2$ and 100 mg/ml BSA. AlkB (final concentration 14 nM) is incubated with increasing concentration of methylated oligonucleotide substrate (2.1-42 mM). The microtiter plate is incubated at 30° C. for 60 minutes. Fifty microliters of Luminos reagent prepared as described in Example 1 is added and the plate is incubated for a further 30 minutes. The signal is then read using a BMG Labtechnologies FluoStar Galaxy in fluorescence intensity mode to detect at 510 nm (±10 nm bandwidth) wavelength with excitation wavelength at 390 nm.

Example 6

Assay of DNA Demethylase Activity

DNA demethylase activity is assayed using methods of the present invention. DNA demethylases, exemplified by human methyl-CpG-binding domain protein 2, can be purified as described in Bhattacharya, S. K. et al., Nature 397 (6720), 579-583, 1999 for use in an inventive assay. Synthetic substrate is generated by in vitro methylation of plasmid DNA. Five micrograms of plasmid DNA is incubated with 8 units of SssI CpG DNA methyltransferase commercially available from New England Biolabs Inc. in a buffer recommended by the manufacturer containing 320 micromolar S-adenosylmethionine, at 37° C. for 2 h as described in Bhattacharya, S. K. et al. The procedure is repeated until full protection from HpaII digestion is observed.

To assay DNA demethylase activity, 5 ng of methylated plasmid is incubated with 1.4 units of the DNA demethylase in buffer containing 20 micrograms of RNase A, for 10 s to 2 h. Luminos reagent solution (50 microliters) is then added to the reaction and the fluorescence is allowed to develop at 37° C. for 30 minutes. The fluorescence of the formaldehyde-Luminos reagent adduct is measured at 510 nm using an excitation wavelength of 440 nm with a Tecan Safire 2 microplate reader.

Example 7

Formaldehyde Detection

Figure 4:
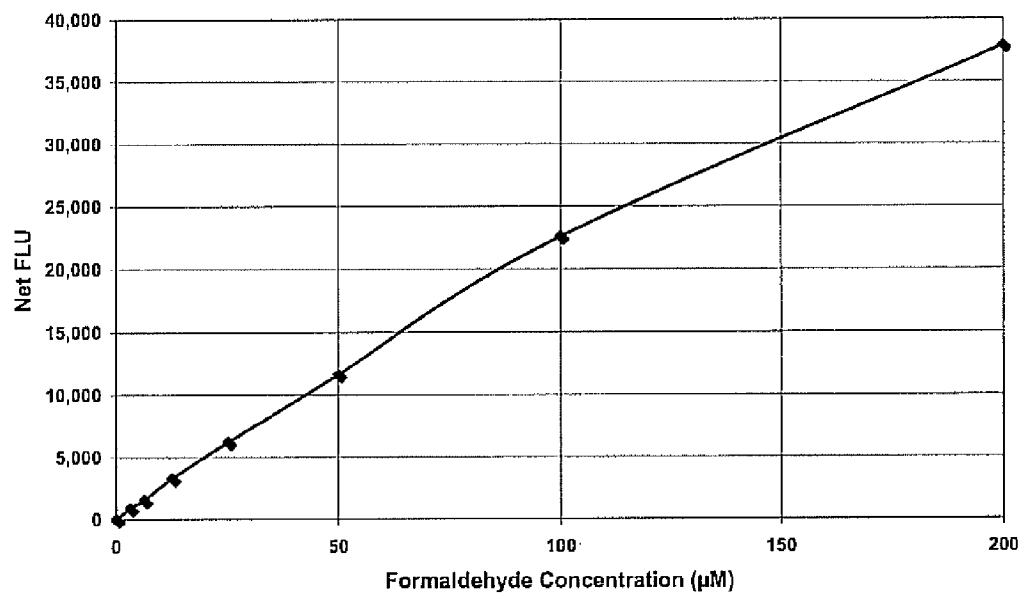
FIG. 4 is a graph showing a formaldehyde standard curve generated using assays and formaldehyde detection reagent according to embodiments of the present invention.

Formaldehyde concentrations in urine obtained from human subjects suspected of exposure to formaldehyde are ascertained using assays according to embodiments of the present invention. Eighteen random clean catch human urine samples are assayed in this example. Human urine is diluted 1:40 with deionized water and 100 µL of the diluted urine is added to the microtiter plate. Formaldehyde standards including 0, 2.5, 5, 10, 25, 50, 100 and 200 micromolar formaldehyde are placed in separate wells of the microtiter plate. 50 µL of Luminos reagent is added to the sample and standards and after a 30 minute incubation at 37° C. the fluorescent signal generated in each well is measured at 510 nm using an excitation wavelength of 440 nm with a Tecan Safire 2 microplate reader. A standard curve generated using known amounts of formaldehyde in this assay is shown in FIG. 4. The fluorescence measured in the sample is compared to the fluorescence measured for the formaldehyde standards. Formaldehyde concentrations in the neat urine samples range from 18 to 776 µM with an average of 225 µM. These samples are also assayed using a urinary creatinine assay kit, which adjusts formaldehyde concentration for urine output, and the formaldehyde levels normalized to creatinine concentration. Normalized values range from 73.0 to 1,026 µmoles formaldehyde/gram creatinine.

Any patents or publications mentioned in this specification are incorporated herein by reference to the same extent as if each individual publication is specifically and individually indicated to be incorporated by reference.

The compositions, methods and kits described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. A method of assaying enzyme-mediated oxidative demethylation, comprising:

combining an oxidative demethylation enzyme, a substrate for the oxidative demethylation enzyme and 4-amino-3-penten-2-one in a reaction mixture under physiological conditions; and detecting fluorescence resulting from reaction of formaldehyde and 4-amino-3-penten-2-one in the reaction mixture under physiological conditions, the formaldehyde generated by oxidative demethylation of the substrate by the enzyme.

2. The method of claim 1, wherein the oxidative demethylation enzyme is selected from the group consisting of: a histone demethylase, a DNA demethylase and a P450 enzyme having demethylase activity.

3. The method of claim 1, wherein the oxidative demethylation enzyme is a human oxidative demethylation enzyme.

4. The method of claim 1, further comprising:

mixing ammonium acetate, acetyl acetone and acetic acid in a solvent, the ammonium acetate added to a concentration in the range of about 0.125M-8M, inclusive, the acetyl acetone added to a concentration in the range of about 0.005M-1.6M, inclusive, and the acetic acid added to a concentration in the range of about 0.0125M-3.2M, inclusive, to produce a formaldehyde detection reagent comprising the 4-amino-3-penten-2-one.

* * * * *

SEQUENCE LISTING

<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: substrate for human JmjD2a
<220> FEATURE:
<221> NAME/KEY: MOD_RES
<222> LOCATION: (9)..(9)
<223> OTHER INFORMATION: METHYLATION, tri-methyl

<400> SEQUENCE: 1

```
Ala Arg Thr Lys Gln Thr Ala Arg Lys Ser Thr Gly Gly Lys Ala
1               5                   10                  15

<210> SEQ ID NO 2
<211> LENGTH: 21
<212> TYPE: PRT
<213> ORGANISM: Artificial Sequence
<220> FEATURE:
<223> OTHER INFORMATION: substrate for histone lysine demethylases
<220> FEATURE:
<221> NAME/KEY: MOD_RES
<222> LOCATION: (4)..(4)
<223> OTHER INFORMATION: METHYLATION, dimethyl

<400> SEQUENCE: 2

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 3
<211> LENGTH: 350
<212> TYPE: PRT
<213> ORGANISM: Homo sapiens

<400> SEQUENCE: 3

Met Ala Ser Glu Ser Glu Thr Leu Asn Pro Ser Ala Arg Ile Met Thr
1               5                   10                  15

Phe Tyr Pro Thr Met Glu Glu Phe Arg Asn Phe Ser Arg Tyr Ile Ala
                20                  25                  30

Tyr Ile Glu Ser Gln Gly Ala His Arg Ala Gly Leu Ala Lys Val Val
            35                  40                  45

Pro Pro Lys Glu Trp Lys Pro Arg Ala Ser Tyr Asp Asp Ile Asp Asp
        50                  55                  60

Leu Val Ile Pro Ala Pro Ile Gln Gln Leu Val Thr Gly Gln Ser Gly
65                  70                  75                  80

Leu Phe Thr Gln Tyr Asn Ile Gln Lys Lys Ala Met Thr Val Arg Glu
                85                  90                  95

Phe Arg Lys Ile Ala Asn Ser Asp Lys Tyr Cys Thr Pro Arg Tyr Ser
            100                 105                 110

Glu Phe Glu Glu Leu Glu Arg Lys Tyr Trp Lys Asn Leu Thr Phe Asn
        115                 120                 125

Pro Pro Ile Tyr Gly Ala Asp Val Asn Gly Thr Leu Tyr Glu Lys His
    130                 135                 140

Val Asp Glu Trp Asn Ile Gly Arg Leu Arg Thr Ile Leu Asp Leu Val
145                 150                 155                 160

Glu Lys Glu Ser Gly Ile Thr Ile Glu Gly Val Asn Thr Pro Tyr Leu
                165                 170                 175

Tyr Phe Gly Met Trp Lys Thr Ser Phe Ala Trp His Thr Glu Asp Met
            180                 185                 190

Asp Leu Tyr Ser Ile Asn Tyr Leu His Phe Gly Glu Pro Lys Ser Trp
        195                 200                 205

Tyr Ser Val Pro Pro Glu His Gly Lys Arg Leu Glu Arg Leu Ala Lys
    210                 215                 220

Gly Phe Phe Pro Gly Ser Ala Gln Ser Cys Glu Ala Phe Leu Arg His
225                 230                 235                 240

Lys Met Thr Leu Ile Ser Pro Leu Met Leu Lys Lys Tyr Gly Ile Pro
                245                 250                 255
```

```
Phe Asp Lys Val Thr Gln Glu Ala Gly Glu Phe Met Ile Thr Phe Pro
            260                 265                 270

Tyr Gly Tyr His Ala Gly Phe Asn His Gly Phe Asn Cys Ala Glu Ser
            275                 280                 285

Thr Asn Phe Ala Thr Arg Arg Trp Ile Glu Tyr Gly Lys Gln Ala Val
290                 295                 300

Leu Cys Ser Cys Arg Lys Asp Met Val Lys Ile Ser Met Asp Val Phe
305                 310                 315                 320

Val Arg Lys Phe Gln Pro Glu Arg Tyr Lys Leu Trp Lys Ala Gly Lys
                325                 330                 335

Asp Asn Thr Val Ile Asp His Thr Leu Pro Thr Pro Glu Ala
            340                 345                 350

<210> SEQ ID NO 4
<211> LENGTH: 702
<212> TYPE: PRT
<213> ORGANISM: Homo sapiens

<400> SEQUENCE: 4

Leu Pro Pro Pro Pro Gln Ala Pro Pro Glu Glu Glu Asn Glu Ser
1               5                   10                  15

Glu Pro Glu Glu Pro Ser Gly Val Glu Gly Ala Ala Phe Gln Ser Arg
                20                  25                  30

Leu Pro His Asp Arg Met Thr Ser Gln Glu Ala Ala Cys Phe Pro Asp
            35                  40                  45

Ile Ile Ser Gly Pro Gln Gln Thr Gln Lys Val Phe Leu Phe Ile Arg
        50                  55                  60

Asn Arg Thr Leu Gln Leu Trp Leu Asp Asn Pro Lys Ile Gln Leu Thr
65                  70                  75                  80

Phe Glu Ala Thr Leu Gln Gln Leu Glu Ala Pro Tyr Asn Ser Asp Thr
                85                  90                  95

Val Leu Val His Arg Val His Ser Tyr Leu Glu Arg His Gly Leu Ile
            100                 105                 110

Asn Phe Gly Ile Tyr Lys Arg Ile Lys Pro Leu Pro Thr Lys Lys Thr
        115                 120                 125

Gly Lys Val Ile Ile Ile Gly Ser Gly Val Ser Gly Leu Ala Ala Ala
130                 135                 140

Arg Gln Leu Gln Ser Phe Gly Met Asp Val Thr Leu Leu Glu Ala Arg
145                 150                 155                 160

Asp Arg Val Gly Gly Arg Val Ala Thr Phe Arg Lys Gly Asn Tyr Val
                165                 170                 175

Ala Asp Leu Gly Ala Met Val Val Thr Gly Leu Gly Gly Asn Pro Met
            180                 185                 190

Ala Val Val Ser Lys Gln Val Asn Met Glu Leu Ala Lys Ile Lys Gln
        195                 200                 205

Lys Cys Pro Leu Tyr Glu Ala Asn Gly Gln Ala Val Pro Lys Glu Lys
210                 215                 220

Asp Glu Met Val Glu Gln Glu Phe Asn Arg Leu Leu Glu Ala Thr Ser
225                 230                 235                 240

Tyr Leu Ser His Gln Leu Asp Phe Asn Val Leu Asn Asn Lys Pro Val
                245                 250                 255

Ser Leu Gly Gln Ala Leu Glu Val Val Ile Gln Leu Gln Glu Lys His
            260                 265                 270

Val Lys Asp Glu Gln Ile Glu His Trp Lys Lys Ile Val Lys Thr Gln
        275                 280                 285
```

```
Glu Glu Leu Lys Glu Leu Leu Asn Lys Met Val Asn Leu Lys Glu Lys
        290             295                 300
Ile Lys Glu Leu His Gln Gln Tyr Lys Glu Ala Ser Glu Val Lys Pro
305             310                 315                 320
Pro Arg Asp Ile Thr Ala Glu Phe Leu Val Lys Ser Lys His Arg Asp
                325                 330                 335
Leu Thr Ala Leu Cys Lys Glu Tyr Asp Glu Leu Ala Glu Thr Gln Gly
            340                 345                 350
Lys Leu Glu Glu Lys Leu Gln Glu Leu Glu Ala Asn Pro Pro Ser Asp
        355                 360                 365
Val Tyr Leu Ser Ser Arg Asp Arg Gln Ile Leu Asp Trp His Phe Ala
    370                 375                 380
Asn Leu Glu Phe Ala Asn Ala Thr Pro Leu Ser Thr Leu Ser Leu Lys
385                 390                 395                 400
His Trp Asp Gln Asp Asp Phe Glu Phe Thr Gly Ser His Leu Thr
                405                 410                 415
Val Arg Asn Gly Tyr Ser Cys Val Pro Val Ala Leu Ala Glu Gly Leu
                420                 425                 430
Asp Ile Lys Leu Asn Thr Ala Val Arg Gln Val Arg Tyr Thr Ala Ser
            435                 440                 445
Gly Cys Glu Val Ile Ala Val Asn Thr Arg Ser Thr Ser Gln Thr Phe
    450                 455                 460
Ile Tyr Lys Cys Asp Ala Val Leu Cys Thr Leu Pro Leu Gly Val Leu
465                 470                 475                 480
Lys Gln Gln Pro Pro Ala Val Gln Phe Val Pro Pro Leu Pro Glu Trp
                485                 490                 495
Lys Thr Ser Ala Val Gln Arg Met Gly Phe Gly Asn Leu Asn Lys Val
            500                 505                 510
Val Leu Cys Phe Asp Arg Val Phe Trp Asp Pro Ser Val Asn Leu Phe
        515                 520                 525
Gly His Val Gly Ser Thr Thr Ala Ser Arg Gly Glu Leu Phe Leu Phe
    530                 535                 540
Trp Asn Leu Tyr Lys Ala Pro Ile Leu Leu Ala Leu Val Ala Gly Glu
545                 550                 555                 560
Ala Ala Gly Ile Met Glu Asn Ile Ser Asp Asp Val Ile Val Gly Arg
                565                 570                 575
Cys Leu Ala Ile Leu Lys Gly Ile Phe Gly Ser Ser Ala Val Pro Gln
                580                 585                 590
Pro Lys Glu Thr Val Val Ser Arg Trp Arg Ala Asp Pro Trp Ala Arg
        595                 600                 605
Gly Ser Tyr Ser Tyr Val Ala Ala Gly Ser Ser Gly Asn Asp Tyr Asp
    610                 615                 620
Leu Met Ala Gln Pro Ile Thr Pro Gly Pro Ser Ile Pro Gly Ala Pro
625                 630                 635                 640
Gln Pro Ile Pro Arg Leu Phe Phe Ala Gly Glu His Thr Ile Arg Asn
                645                 650                 655
Tyr Pro Ala Thr Val His Gly Ala Leu Leu Ser Gly Leu Arg Glu Ala
            660                 665                 670
Gly Arg Ile Ala Asp Gln Phe Leu Gly Ala Met Tyr Thr Leu Pro Arg
        675                 680                 685
Gln Ala Thr Pro Gly Val Pro Ala Gln Gln Ser Pro Ser Met
690                 695                 700
```